(12) United States Patent
Bonfanti et al.

(10) Patent No.: US 7,884,215 B2
(45) Date of Patent: Feb. 8, 2011

(54) 2-SUBSTITUTED BENZIMIDAZOLES

(76) Inventors: Jean-François Bonfanti, 11 Impasse des Lauriers, 27430 Andé (FR); Philippe Muller, 17 Route d'Herqueville, 27430 Andé (FR); Jérôme Michel Claude Fortin, 22, rue des acacias, 27460 Igoville (FR); Frédéric Marc Maurice Doublet, 1646, Route de Neufchatel, 76230 Isneauville (FR)

( * ) Notice: Subject to any disclaimer, the term of this patent is extended or adjusted under 35 U.S.C. 154(b) by 624 days.

(21) Appl. No.: 11/993,136

(22) PCT Filed: Jun. 20, 2006

(86) PCT No.: PCT/EP2006/063367

§ 371 (c)(1),
(2), (4) Date: Dec. 19, 2007

(87) PCT Pub. No.: WO2006/136563

PCT Pub. Date: Dec. 28, 2006

(65) Prior Publication Data

US 2010/0092426 A1    Apr. 15, 2010

(30) Foreign Application Priority Data

Jun. 20, 2005    (EP)    ................... 05076440

(51) Int. Cl.
*C07D 295/00*    (2006.01)
(52) U.S. Cl. .................................. 548/309.7
(58) Field of Classification Search .................. 514/394; 548/309.7
See application file for complete search history.

(56) References Cited

FOREIGN PATENT DOCUMENTS

| WO | WO 01/00611 A | 1/2001 |
|---|---|---|
| WO | WO 01/00612 A | 1/2001 |
| WO | WO 01/095910 | 12/2001 |
| WO | 02/092575 | * 11/2002 |
| WO | WO 02/092575 A | 11/2002 |

\* cited by examiner

*Primary Examiner*—James O Wilson
*Assistant Examiner*—Erich A Leeser

(57) ABSTRACT

Inhibitors of RSV replication of formula (I) the addition salts and stereochemically isomeric forms thereof, wherein Q is hydrogen, $C_{1-6}$alkyl optionally substituted with a heterocycle or Q is $C_{1-6}$alkyl substituted with both —$OR^4$ and a heterocycle; wherein said heterocycle is oxazolidine, thiazolidine, 1-oxo-thiazolidine, 1,1-dioxothiazolidine, morpholinyl, thiomorpholinyl, 1-oxo-thiomorpholinyl, 1,1-dioxothiomorpholinyl, hexahydrooxazepine, hexahydro-thiazepine, 1-oxo-hexahydrothiazepine, 1,1-dioxo-hexahydrothiazepine, pyrrolidine, piperidine, homopiperidine, piperazine; which heterocyle may be substituted with 1-2 substituents; each Alk is $C_{1-6}$alkanediyl; $R^1$ is $Ar^2$ or optionally substituted piperidinyl, piperazinyl, morpholinyl, thiomorpholinyl, pyridyl, pyrazinyl, pyridazinyl, pyrimidinyl, furanyl, tetrahydro-furanyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]pyridinyl or 2,3-dihydro-1,4-dioxino[2,3-b]pyridyl; $R^3$ is hydroxy$C_{1-6}$alkyl, $C_{1-6}$alkoxy$C_{1-6}$alkyl, cyano$C_{1-6}$alkyl, aminocarbonyl-$C_{1-6}$-alkyl, mono- or di($C_{1-6}$alkyl)aminocarbonyl-$C_{1-6}$-alkyl, carboxyl-$C_{1-6}$-alkyl, $C_{1-6}$alkoxycarbonyl-$C_{1-6}$alkyl; $R^2$ is hydrogen or $C_{1-6}$alkyl; $R^3$ and $R^4$ are hydrogen, $C_{1-6}$alkyl, $Ar^2$, $Ar^2C_{1-6}$alkyl, $C_{1-6}$alkylcarbonyl, $Ar^2$carbonyl, $Ar^2C_{1-6}$alkylcarbonyl, $C_{1-6}$alkylsulfonyl, aminosulfonyl, $Ar^1$sulfonyl, $Ar^1C_{1-6}$alkylsulfonyl, $C_{1-6}$alkyloxy$C_{1-6}$alkyl, amino$C_{1-6}$alkyl, mono- or di($C_{1-6}$alkyl)-amino$C_{1-6}$alkyl, hydroxy$C_{1-6}$alkyl, aminocarbonyl$C_{1-6}$alkyl, $C_{1-4}$alkyloxycarbonyl-$C_{1-6}$alkyl, hydroxycarbonyl$C_{1-6}$alkyl, aminosulfonyl$C_{1-6}$alkyl, Het, Het-$C_{1-6}$alkyl, Het-carbonyl, Het-sulfonyl, Het$C_{1-6}$alkylsulfonyl, Het-$C_{1-6}$alkylcarbonyl; Het is an optionally substituted heterocycle; pharmaceutical compositions containing compounds (I) and processes for preparing compounds (I).

10 Claims, No Drawings

2-SUBSTITUTED BENZIMIDAZOLES

The present invention is concerned with 2-substituted benzimidazoles having inhibitory activity on the replication of the respiratory syncytial virus (RSV). It further concerns compositions comprising these compounds as active ingredient as well as processes for preparing these compounds and compositions.

Human RSV or Respiratory Syncytial Virus is a large RNA virus, member of the family of Paramyxoviridae, subfamily pneumovirinae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue, provides an aerosol treatment for serious RSV infection in hospitalized children. The aerosol route of administration, the toxicity (risk of teratogenicity), the cost and the highly variable efficacy limit its use. The other two drugs, RespiGam® and palivizumab, polyclonal and monoclonal antibody immunostimulants, are intended to be used in a preventive way.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication.

Groups of benzimidazoles and imidazopyridines have been described in WO-01/00611, WO-01/00612 and WO-01/00615 as inhibitors of RSV replication. The compounds of the present invention differ from these prior art compounds both in terms of chemical structure and activity profile.

The present invention concerns inhibitors of RSV replication, which can be represented by formula (I)

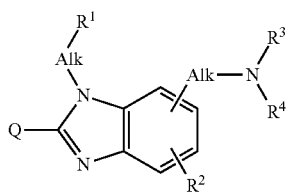

(I)

the addition salts and stereochemically isomeric forms thereof, wherein

Q is hydroxy, $C_{1-6}$alkyloxy, $C_{1-6}$alkylcarbonylamino, $C_{1-6}$alkyloxycarbonylamino, carboxyl, $C_{1-6}$alkyloxycarbonyl, $C_{1-6}$alkylcarbonyl, cyano, aminocarbonyl, mono or di($C_{1-6}$alkyl)aminocarbonyl, polyhalo$C_{1-6}$alkyl;

each Alk independently represents $C_{1-6}$alkanediyl;

$R^1$ is $Ar^2$ or a monocyclic or bicyclic heterocycle selected from piperidinyl, piperazinyl, morpholinyl, thiomorpholinyl, pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]-pyridinyl, imidazo[1,2-a]pyridinyl and 2,3-dihydro-1,4-dioxino[2,3-b]pyridyl; wherein each of said monocyclic or bicyclic heterocycles may optionally be substituted with 1, 2, or 3 substituents each independently selected from the group consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyloxycarbonyl, aminocarbonyl, mono- and di$C_{1-6}$alkylaminocarbonyl;

$R^2$ is hydrogen or $C_{1-6}$alkyl;

$R^3$ and $R^4$ independently from each other are hydrogen, $C_{1-6}$alkyl, $Ar^2$, $Ar^2C_{1-6}$alkyl, $C_{1-6}$alkylcarbonyl, $Ar^2$carbonyl, $Ar^2C_{1-6}$alkylcarbonyl, $C_{1-6}$alkylsulfonyl, aminosulfonyl, $Ar^1$sulfonyl, $Ar^1C_{1-6}$alkylsulfonyl, $C_{1-6}$alkyloxy$C_{1-6}$alkyl, amino$C_{1-6}$alkyl, mono- or di($C_{1-6}$alkyl)amino$C_{1-6}$alkyl, hydroxy$C_{1-6}$alkyl, aminocarbonyl$C_{1-6}$alkyl, $C_{1-6}$alkyloxycarbonyl$C_{1-6}$alkyl, hydroxycarbonyl-$C_{1-6}$alkyl, aminosulfonyl$C_{1-6}$alkyl, Het, Het-$C_{1-6}$alkyl, Het-carbonyl, Het-sulfonyl, Het$C_{1-6}$alkylsulfonyl and Het-$C_{1-6}$alkylcarbonyl;

$Ar^1$ is phenyl or phenyl substituted with 1 or more, such as 2, 3 or 4, substituents selected from halo, hydroxy, $C_{1-6}$alkyl, hydroxy$C_{1-6}$alkyl, polyhalo$C_{1-6}$alkyl, and $C_{1-6}$alkyloxy;

$Ar^2$ is phenyl or phenyl substituted with 1 or more, such as 2, 3, 4 or 5, substituents selected from halo, cyano, $C_{1-6}$alkyl, $C_{2-6}$alkenyl, $C_{2-6}$alkynyl, cyano$C_{1-6}$alkyl, cyano$C_{2-6}$alkenyl, cyano$C_{2-6}$alkynyl, $Ar^1$, $Ar^1C_{1-6}$alkyl, $R^{5b}$—O—, $R^{5b}$—S—, —N($R^{5a}R^{5b}$), polyhalo$C_{1-6}$alkyl, polyhalo$C_{1-6}$alkyloxy, $R^6$—C(=O)—, $R^{5b}$—O—C(=O)—, N($R^{5a}R^{5b}$)—C(=O)—, N($R^{5a}R^{5b}$)-sulfonyl, $R^{5b}$—O—$C_{1-6}$alkyl, $R^{5b}$—S—$C_{1-6}$alkyl, $R^6$—S(=O)$_2$—$C_{1-6}$alkyl, N($R^{5a}R^{5b}$)—$C_{1-6}$alkyl, $R^6$—C(=O)—$C_{1-6}$alkyl, $R^{5b}$—O—C(=O)—$C_{1-6}$alkyl, N($R^{5a}R^{5b}$)—C(=O)—$C_{1-6}$alkyl, $R^6$—C(=O)—NR$^{5b}$—, $R^6$—S(=O)$_2$-amino, $R^6$—C(=O)—O—, $R^6$—C(=O)—NR$^{5b}$—$C_{1-6}$alkyl, $R^6$—C(=O)—O—$C_{1-6}$alkyl;

$R^{5a}$ is hydrogen, $C_{1-6}$alkyl, $Ar^1$, $Ar^1C_{1-6}$alkyl, $C_{1-6}$alkylcarbonyl, $Ar^1$carbonyl, $Ar^1C_{1-6}$alkylcarbonyl, $C_{1-6}$alkylsulfonyl, $Ar^1$sulfonyl, $Ar^1C_{1-6}$alkylsulfonyl, amino$C_{1-6}$alkyl, mono- or di($C_{1-6}$alkyl)amino$C_{1-6}$alkyl, hydroxy$C_{1-6}$alkyl, Het, Het-$C_{1-6}$alkyl, Het-carbonyl, Het-sulfonyl, Het-$C_{1-6}$alkylcarbonyl;

$R^{5b}$ is hydrogen, $C_{1-6}$alkyl, $Ar^1$ or $Ar^1C_{1-6}$alkyl;

$R^6$ is $C_{1-6}$alkyl, $Ar^1$ or $Ar^1C_{1-6}$alkyl;

Het is a heterocycle being selected from tetrahydrofuranyl, tetrahydrothienyl, pyrrolidinyl, pyrrolidinonyl, furanyl, thienyl, pyrrolyl, thiazolyl, oxazolyl, imidazolyl, isothiazolyl, pyrazolyl, isoxazolyl, oxadiazolyl, thiadiazolyl, piperidinyl, homopiperidinyl, piperazinyl, morpholinyl, pyridyl, pyrazinyl, pyridazinyl, pyrimidinyl, tetrahydroquinolinyl, quinolinyl, isoquinolinyl, benzodioxanyl, benzodioxolyl, indolinyl, indolyl, each of said heterocycle may optionally be substituted with oxo, amino, $Ar^1$, $Ar^1C_{1-6}$ alkyl, mono- or di($C_{1-6}$alkyl)amino$C_{1-6}$alkyl, mono- or di($C_{1-6}$alkyl)amino, hydroxy$C_{1-6}$alkyl, $C_{1-6}$alkoxy$C_{1-6}$ alkyl, cyano$C_{1-6}$alkyl, aminocarbonyl-$C_{1-6}$-alkyl, mono- or di($C_{1-6}$alkyl)aminocarbonyl-$C_{1-6}$-alkyl, carboxyl-$C_{1-6}$-alkyl, $C_{1-6}$alkoxycarbonyl-$C_{1-6}$alkyl;

The invention also relates to the use of a compound of formula (I), or an addition salt or a stereochemically isomeric form thereof, for the manufacture of a medicament for inhibiting RSV replication. Or the invention relates to a method of inhibiting RSV replication in a warm-blooded animal said method comprising the administration of an effective amount of a compound of formula (I), or an addition salt or a stereochemically isomeric form thereof.

As used in the foregoing and hereinafter, "polyhalo$C_{1-6}$alkyl" as a group or part of a group, e.g. in polyhalo$C_{1-6}$alkyloxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoro $C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo-$C_{1-4}$alkyl, the halogen atoms may be the same or different.

Each Ar may be unsubstituted phenyl or phenyl substituted with 1 to 5 substituents, such as 5 or 4 substituents or, which is preferred, up to 3 substituents, or up to two substituents, or with one substituent.

A hydroxy$C_{1-6}$alkyl group when substituted on an oxygen atom or a nitrogen atom preferably is a hydroxy$C_{2-6}$alkyl group wherein the hydroxy group and the oxygen or nitrogen are separated by at least two carbon atoms.

As used herein "$C_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_{2-6}$alkenyl is $C_{2-4}$alkenyl.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-pentynyl, 3-pentynyl, 2-hexynyl, 3-hexynyl and the like. Of interest amongst $C_{2-6}$alkynyl is $C_{2-4}$alkynyl.

$C_{3-7}$cycloalkyl is generic to cyclopropyl, cyclobutyl, cyclopentyl, cyclohexyl and cycloheptyl.

$C_{1-6}$alkanediyl defines bivalent straight and branched chain saturated hydrocarbon radicals having from 1 to 6 carbon atoms such as, for example, methylene, ethylene, 1,3-propanediyl, 1,4-butanediyl, 1,2-propanediyl, 2,3-butanediyl, 1,5-pentanediyl, 1,6-hexanediyl and the like. Of interest amongst $C_{1-6}$alkanediyl is $C_{1-4}$alkanediyl.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar term is meant to include the compounds of formula (I), their addition salts and stereochemically isomeric forms.

Some of the compounds of formula (I) may contain one or more centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), or their salts, and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g. halogen or $C_{1-4}$alkyl) occurs more than one time in any constituent, each definition is independent.

The term "compounds of formula (I)", or any similar terms such as "compounds of the invention" and the like, is meant to also comprise any prodrugs that the compounds of formula (I) may form. The term "prodrug" as used herein is meant to comprise any pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, $8^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-only-methyl; and $C_{1-6}$alkoxycarbonyloxyethyl esters for example 1-methoxycarbonyloxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring. Alkanoyl esters for example are any $C_{1-30}$alkanoyl esters, in particular $C_{8-30}$alkanoyl esters, more in particular $C_{10-24}$alkanoyl esters, further in particular $C_{16-20}$alkanoyl esters, wherein the alkyl part may have one or more double bonds. Examples of alkanoyl esters are decanoate, palmitate and stearate.

The term "compounds of formula (I)", or any similar terms such as "compounds of the invention" and the like, is meant to also comprise any metabolites that are formed in vivo upon administration of the drug. Some examples of metabolites in accordance with the invention include, but are not limited to, (a) where the compound of formula (I) contains a methyl group, a hydroxymethyl derivative thereof; (b) where the compound of formula (I) contains an alkoxy group, an hydroxy derivative thereof; (c) where the compound of formula (I) contains a tertiary amino group, a secondary amino derivative thereof; (d) where the compound of formula (I) contains a secondary amino group, a primary derivative thereof; (e) where the compound of formula (I) contains a phenyl moiety, a phenol derivative thereof; and (f) where the compound of formula (I) contains an amide group, a carboxylic acid derivative thereof.

The term "compounds of formula (I)", or any similar terms such as "compounds of the invention" and the like, is meant to also comprise any N-oxide forms of the compounds of formula (I), which are compounds of formula (I) wherein one or several nitrogen atoms are oxidized to the N-oxide form.

The term "compounds of formula (I)", or any similar terms such as "compounds of the invention" and the like, is meant to also comprise the metal complexes or chelates of the compounds of formula (I) in particular with physiologically acceptable metal ions e.g. Mg, Ca, Fe, Zn ions.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates, which the compounds of formula (I) as well as the salts thereof, are able to form. Such solvates are for example hydrates, alcoholates and the like.

Some of the compounds of formula (I) may also exist in their tautomeric form. Such forms although not explicitly indicated in the above formula are intended to be included within the scope of the present invention.

One embodiment of the present invention concerns compounds of formula (I-a):

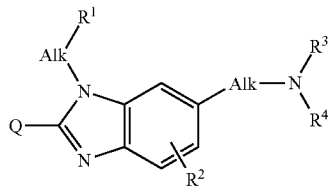

(I-a)

Another embodiment of the present invention concerns compounds of formula (I-b):

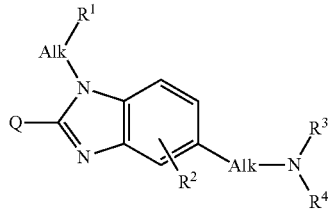

(I-b)

In (I-a) and (I-b) Q, Alk, $R^1$, $R^2$, $R^3$, $R^4$ are as specified in the definitions of the compounds of formula (I) or of any of the subgroups of compounds of formula (I) specified herein.

One embodiment of the present invention concerns compounds of formula (I-a-1):

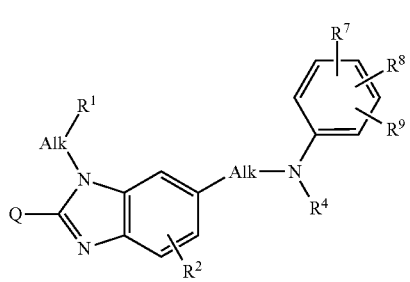

(I-a-1)

Another particular embodiment of the present invention concerns compounds of formula (I-b-1):

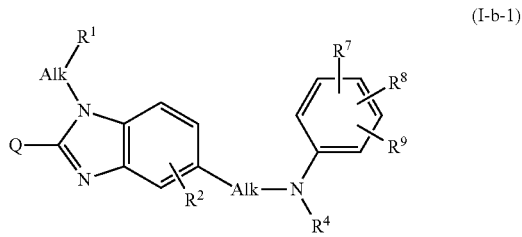

(I-b-1)

In (I-a-1) and (I-a-2) Q, Alk, $R^1$, $R^2$ and $R^4$ are as specified in the definitions of the compounds of formula (I) or any of the subgroups of compounds of formula (I) specified herein; and $R^7$, $R^8$, $R^9$ independently from one another have the same meanings as the substituents on $Ar^2$ as specified in the definitions of the compounds of formula (I) or of any of the subgroups thereof.

It is to be understood that the above defined subgroups of compounds of formulae (I-a), (I-b), (I-a-1), (I-b-1) as well as any other subgroup defined herein, are meant to also comprise any addition salts and stereochemically isomeric forms of such compounds.

In (I-a-1) and (I-b-1) the radicals
(a) $R^7$, $R^8$, $R^9$ preferably and independently from one another are $C_{1-6}$alkyl or $R^{5b}$—O—$C_{1-6}$alkyl; and $R^8$ and/or $R^9$ may also be hydrogen; or
(b) $R^7$, $R^8$ more preferably and independently from one another are $C_{1-6}$alkyl or $R^{5b}$—O—$C_{1-6}$alkyl; and $R^9$ is hydrogen; or
(c) $R^7$, $R^8$ still more preferably are $C_{1-6}$alkyl and $R^9$ is hydrogen; or
(d) $R^7$ is $C_{1-6}$alkyl, $R^8$ is $R^{5b}$—O—$C_{1-6}$alkyl and $R^9$ is hydrogen.

In (a)-(d), $R^{5b}$ is as defined in the definitions of the compounds of formula (I) or any of the subgroups thereof.

Subgroups I of the compounds of formula (I) are those compounds of formula (I), or any subgroup of compounds of formula (I) specified herein, wherein one or both of the radicals Alk is ethylene or methylene, more in particular wherein one or both of the radicals Alk is methylene.

Subgroups II of the compounds of formula (I) are those compounds of formula (I), or any subgroup of compounds of formula (I) specified herein, such as the subgroups I mentioned above, wherein
(a) $R^1$ is $Ar^2$ or a heterocycle selected from pyridyl, pyrazinyl, pyridazinyl, pyrimidinyl, furanyl, thienyl, pyrrolyl, oxazolyl, imidazolyl, isothiazolyl, pyrazolyl, isoxazolyl, quinolinyl, benzofuranyl, benzimidazolyl, benzoxazolyl, benzthiazolyl; wherein each of said heterocycle may optionally be substituted with 1, 2, or 3 substituents each independently selected from the group consisting of halo, hydroxy, amino, cyano, carboxyl, $C_{1-6}$alkyl, $C_{1-6}$alkyloxy, $C_{1-6}$alkyloxy-$C_{1-6}$alkyl, hydroxyl$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkyloxycarbonyl, aminocarbonyl, mono- and di-$C_{1-6}$alkylaminocarbonyl;
(b) $R^1$ is $Ar^2$, or a heterocycle selected from quinolinyl, benzimidazolyl, pyrazinyl or pyridyl; wherein each of said heterocycle may optionally be substituted with 1, 2, or 3 substituents each independently selected from the group consisting of halo, hydroxy, amino, cyano, carboxyl, $C_{1-6}$alkyl, $C_{1-6}$alkyloxy, $C_{1-6}$alkyloxy$C_{1-6}$alkyl, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkyloxycarbonyl, aminocarbonyl, mono- and di-C$_{1-6}$ alkylaminocarbonyl;

(c) R$^1$ is Ar$^2$, quinolinyl, benzimidazolyl, pyrazinyl or pyridyl, wherein each of these radicals may optionally be substituted with one, two or three radicals selected from the group consisting of halo, hydroxy, C$_{1-6}$alkyl, C$_{1-6}$alkyloxy;

(d) R$^1$ is phenyl optionally substituted with one, two or three radicals selected from the group consisting of halo, hydroxy, C$_{1-6}$alkyl, C$_{1-6}$alkyloxy; quinolinyl; benzimidazolyl optionally substituted with C$_{1-6}$alkyl; pyridyl optionally substituted with one or two radicals selected from hydroxy, halo, C$_1$ alkyl, benzyloxy and C$_{1-6}$alkyloxy, pyrazinyl optionally substituted with up to three radicals selected from C$_{1-6}$alkyl; or pyridyl substituted or optionally substituted as specified above in (a)-(i); or wherein (e) R$^1$ is phenyl optionally substituted with one or two radicals selected from the group consisting of halo, hydroxy, C$_{1-6}$alkyl, C$_{1-6}$alkyloxy;

(f) R$^1$ is pyrazinyl optionally substituted with up to three radicals selected from C$_{1-6}$alkyl.

(g) R$^1$ is pyridyl substituted with 1 or 2 substituents independently selected from the group consisting of hydroxy, C$_{1-6}$alkyl, halo, C$_{1-6}$alkyloxy, Ar$^1$C$_{1-6}$alkyloxy and (C$_{1-6}$alkyloxy)C$_{1-6}$alkyloxy;

(h) R$^1$ is pyridyl substituted with 1 or 2 substituents independently selected from the group consisting of hydroxy, C$_1$ alkyl, halo and C$_{1-6}$alkyloxy;

(i) R$^1$ is pyridyl substituted with 1 or 2 substituents independently selected from the group consisting of hydroxy and C$_{1-6}$alkyl;

(j) R$^1$ is pyridyl substituted with hydroxy and C$_{1-6}$alkyl.

The group Ar$^2$ in the definitions of R$^1$ may also be phenyl or phenyl substituted with 1 to 5, such as 1, 2, 3 or 4, substituents selected from halo, hydroxy, amino, mono- or di(C$_{1-6}$ alkyl)amino, C$_{1-6}$alkylcarbonylamino, C$_{1-6}$alkylsulfonylamino, cyano, C$_{2-6}$alkenyl, C$_{2-6}$alkynyl, phenyl, hydroxyC$_{1-6}$alkyl, polyhaloC$_{1-6}$alkyl, aminoC$_{1-6}$alkyl, mono- or di(C$_{1-6}$alkyl)aminoC$_{1-6}$alkyl, C$_{1-6}$alkyloxy, polyhaloC$_{1-6}$alkyloxy, phenoxy, aminocarbonyl, mono- or di(C$_{1-6}$alkyl)aminocarbonyl, hydroxycarbonyl, C$_{1-6}$alkoxycarbonyl, C$_{1-6}$alkylcarbonyl, aminosulfonyl, mono- and di(C$_{1-6}$alkyl)aminosulfonyl.

The group Ar$^2$ in the definitions of R$^1$ may also be Ar$^1$ i.e. phenyl or phenyl substituted with 1 or more, such as 2, 3 or 4, substituents selected from halo, hydroxy, C$_{1-6}$alkyl, hydroxyC$_{1-6}$alkyl, polyhaloC$_{1-6}$alkyl, and C$_{1-6}$alkyloxy.

Embodiments of the invention are compounds of formula (I) or any of the subgroups of compounds of formula (I) wherein Alk is methylene and R$^1$ is as specified above in (a)-(j).

Subgroups III of the compounds of formula (I) are those compounds of formula (I), or any subgroup of compounds of formula (I) specified herein, such as the subgroups I and II mentioned above, wherein R$^2$ is hydrogen.

Subgroups IV of the compounds of formula (I) are those compounds of formula (I), or any subgroup of compounds of formula (I) specified herein, such as the subgroups I, II and III mentioned above, wherein (a) R$^3$ and R$^4$ are each independently selected from hydrogen, C$_{1-6}$alkyl, Ar$^2$, Ar$^2$C$_{1-6}$alkyl, C$_{1-6}$alkylcarbonyl, Ar$^2$carbonyl, Ar$^2$C$_{1-6}$alkylcarbonyl, Ar$^1$C$_{1-6}$alkylsulfonyl, C$_{1-6}$alkyloxyC$_{1-6}$alkyl, aminoC$_{1-6}$alkyl, mono- or di(C$_{1-6}$alkyl)aminoC$_{1-6}$alkyl, hydroxyC$_{1-6}$alkyl, aminocarbonylC$_{1-6}$alkyl, C$_{1-6}$alkyloxycarbonylC$_{1-6}$alkyl, hydroxycarbonylC$_{1-6}$alkyl, aminosulfonylC$_{1-6}$alkyl, Het, Het-C$_1$ alkyl; or (b) R$^3$ and R$^4$ are each independently selected from hydrogen, C$_{1-6}$ alkyl, Ar$^2$, Ar$^2$C$_{1-6}$alkyl, C$_{1-6}$alkylcarbonyl, Ar$^2$carbonyl, Ar$^2$C$_{1-6}$alkylcarbonyl, C$_{1-6}$alkyloxyC$_{1-6}$alkyl, aminoC$_{1-6}$alkyl, mono- or di(C$_{1-6}$alkyl)aminoC$_{1-6}$alkyl, hydroxyC$_{1-6}$alkyl, aminocarbonylC$_{1-6}$alkyl, C$_{1-6}$alkyloxycarbonylC$_{1-6}$alkyl, hydroxycarbonylC$_{1-6}$alkyl, aminosulfonylC$_{1-6}$alkyl, Het, Het-C$_{1-6}$alkyl;

(c) R$^3$ and R$^4$ are each independently selected from hydrogen, morpholinyl-C$_{1-6}$alkyl, hydroxyC$_{1-6}$alkyl, (C$_{1-6}$alkyloxy)C$_{1-6}$alkyl, aminoC$_{1-6}$alkyl, mono- and di(C$_{1-6}$alkyl)aminoC$_{1-6}$alkyl, carboxylC$_{1-6}$alkyl, aminocarbonylC$_{1-6}$alkyl, mono- and di(C$_{1-6}$alkyl)aminocarbonylC$_{1-6}$alkyl, aminosulfonyl-C$_{1-6}$alkyl, mono- and di(C$_{1-6}$alkyl)aminosulfonyl-C$_{1-6}$alkyl and Ar$^1$; or wherein (d) R$^3$ and R$^4$ are each independently selected from hydrogen, hydroxyC$_{1-6}$alkyl, (C$_{1-6}$alkyloxy)C$_{1-6}$alkyl, aminoC$_{1-6}$alkyl, mono- and di(C$_{1-6}$alkyl)aminoC$_{1-6}$alkyl, carboxylC$_{1-6}$alkyl, aminocarbonylC$_{1-6}$alkyl, mono- and di(C$_{1-6}$alkyl)aminocarbonyl-C$_{1-6}$alkyl, Ar$^2$; or wherein (e) R$^3$ and R$^4$ are each independently selected from hydrogen, hydroxyC$_{1-6}$alkyl, aminocarbonylC$_{1-6}$alkyl, mono- and di(C$_{1-6}$alkyl)aminocarbonylC$_{1-6}$alkyl, Ar$^2$; or wherein (f) R$^3$ and R$^4$ are each independently selected from hydrogen, hydroxyC$_{1-6}$alkyl and aminocarbonylC$_{1-6}$alkyl, Ar$^2$.

Further embodiments of the invention are compounds of formula (I) or any of the subgroups of compounds of formula (I) wherein R$^3$ is as specified in the definitions of the compounds of formula (I) or as in (a)-(f) in the previous paragraph and R$^4$ is Ar$^2$.

Further embodiments of the invention are compounds of formula (I) or any of the subgroups of compounds of formula (I) wherein R$^3$ is hydrogen and R$^4$ is Ar$^2$.

The group Ar$^2$ in the definitions of R$^3$ and R$^4$ may also be phenyl or phenyl substituted with 1 to 5, such as 1, 2, 3 or 4, substituents selected from halo, hydroxy, amino, mono- or di(C$_{1-6}$alkyl)amino, C$_{1-6}$alkylcarbonylamino, C$_{1-6}$alkylsulfonylamino, cyano, C$_{1-6}$alkyl, C$_{2-6}$alkenyl, C$_{2-6}$alkynyl, phenyl, hydroxyC$_{1-6}$alkyl, polyhaloC$_{1-6}$alkyl, aminoC$_{1-6}$alkyl, mono- or di(C$_{1-6}$alkyl)aminoC$_{1-6}$alkyl, C$_{1-6}$alkyloxy, polyhalo-C$_{1-6}$alkyloxy, phenoxy, aminocarbonyl, mono- or di(C$_{1-6}$ alkyl)aminocarbonyl, hydroxycarbonyl, C$_{1-6}$alkoxycarbonyl, C$_{1-6}$alkylcarbonyl, aminosulfonyl, mono- and di(C$_{1-6}$alkyl)aminosulfonyl.

The group Ar$^2$ in the definitions of R$^3$ and R$^4$ may also be Ar$^1$ i.e. phenyl or phenyl substituted with 1 or more, such as 2, 3 or 4, substituents selected from halo, hydroxy, C$_{1-6}$alkyl, hydroxyC$_{1-6}$alkyl, polyhaloC$_{1-6}$alkyl, and C$_{1-6}$alkyloxy.

The group Ar$^2$ in the radicals Ar$^2$C$_{1-6}$alkyl, Ar$^2$carbonyl, Ar$^2$C$_{1-6}$alkylcarbonyl in the definitions of R$^3$ and R$^4$ may also be Ar$^1$.

Subgroups V of the compounds of formula (I) are those compounds of formula (I), or any subgroup of compounds of formula (I) specified herein, such as the subgroups I, II, III and IV mentioned above, wherein (a) R$^{5a}$ is hydrogen, C$_{1-6}$alkyl, Ar$^1$, Ar$^1$C$_{1-6}$alkyl, C$_{1-6}$alkylcarbonyl, Ar$^1$carbonyl, Ar$^1$C$_{1-6}$alkylcarbonyl, C$_{1-6}$alkylsulfonyl, Ar$^1$sulfonyl, Ar$^1$C$_{1-6}$alkylsulfonyl, C$_{1-6}$alkyloxyC$_{1-6}$alkyl, aminoC$_{1-6}$alkyl, mono- or di(C$_{1-6}$alkyl)aminoC$_{1-6}$alkyl, hydroxyC$_{1-6}$alkyl, Het, Het-C$_{1-6}$alkyl;

(b) R$^{5a}$ is hydrogen, C$_{1-6}$alkyl, Ar$^1$, Ar$^1$C$_{1-6}$alkyl, C$_{1-6}$alkylcarbonyl, Ar$^1$carbonyl, Ar$^1$C$_{1-6}$alkylcarbonyl, C$_{1-6}$alkyloxyC$_{1-6}$alkyl, aminoC$_{1-6}$alkyl, mono- or di(C$_{1-6}$alkyl)aminoC$_{1-6}$alkyl, hydroxyC$_{1-6}$alkyl;

(c) $R^{5a}$ is hydrogen, $C_{1-6}$alkyl, $Ar^1$, $C_{1-6}$alkylcarbonyl, $Ar^1$carbonyl, amino$C_{1-6}$alkyl, hydroxy$C_{1-6}$alkyl;

(d) $R^{5a}$ is hydrogen, $C_{1-6}$alkyl, $Ar^1C_{1-6}$alkyl;

(e) $R^{5a}$ is hydrogen, $C_{1-6}$alkyl; or (f) $R^{5a}$ is hydrogen, $C_{1-6}$alkyl.

Subgroups VI of the compounds of formula (I) are those compounds of formula (I), or any subgroup of compounds of formula (I) specified herein, such as the subgroups I, II, III, N and V mentioned above, wherein (a) $R^{5a}$ is hydrogen, $C_{1-6}$alkyl, or $Ar^1C_{1-6}$alkyl; or (b) $R^{5b}$ is hydrogen.

Subgroups VII of the compounds of formula (I) are those compounds of formula (I), or any subgroup of compounds of formula (I) specified herein, such as the subgroups I, II, III, IV, V and VI mentioned above, wherein $R^6$ is $C_{1-6}$alkyl Subgroups VIII of the compounds of formula (I) are those compounds of formula (I), or any subgroup of compounds of formula (I) specified herein, such as the subgroups I, II, III, IV, V, VI and VII mentioned above, wherein (a) Q is hydroxy, $C_{1-6}$alkylcarbonylamino, carboxyl, $C_{1-6}$alkyloxycarbonyl, $C_{1-6}$alkylcarbonyl, cyano, aminocarbonyl, mono or di($C_{1-6}$alkyl)aminocarbonyl, polyhalo$C_{1-6}$alkyl;

(b) Q is hydroxy, $C_{1-6}$alkylcarbonylamino, carboxyl, $C_{1-6}$alkyloxycarbonyl, $C_{1-6}$alkylcarbonyl, cyano, aminocarbonyl, mono or di($C_{1-6}$alkyl)aminocarbonyl, polyhalo$C_{1-6}$alkyl; or (c) Q is hydroxy, $C_{1-6}$alkylcarbonylamino, carboxyl.

Embodiments of the invention are those compounds of formula (I) or compounds belonging to any of the subgroups of compounds of formula (I) specified herein, wherein one or more of $Ar^1$ or $Ar^2$ is phenyl or phenyl substituted with 1, 2, 3 substituents or with 1, 2 substituents selected from those mentioned in the definition of the compounds of formula (I) or of any subgroup thereof.

Subgroups IX of the compounds of formula (I) are those compounds of formula (I), or any subgroup of compounds of formula (I) specified herein, such as the subgroups I, II, III, IV, V, VI, VII and VIII mentioned above, wherein (a) one or more of $Ar^2$ is phenyl or phenyl substituted with up to 3 substituents, or with up to 2 substituents, or with one substituent, selected from the group consisting of halo, hydroxy, amino, cyano, $C_{1-6}$alkyl, hydroxy$C_{1-6}$alkyl, polyhalo$C_{1-6}$alkyl, amino$C_{1-6}$alkyl, $C_{1-6}$alkyloxy, aminosulfonyl, aminocarbonyl, hydroxycarbonyl, $C_{1-6}$alkylcarbonyl, mono- or di($C_{1-6}$alkyl)amino and $C_{1-6}$alkoxycarbonyl; or (b) one or more of $Ar^2$ is phenyl or phenyl substituted with up to 3 substituents, or with up to 2 substituents, or with one substituent, selected from the group consisting of halo, hydroxy, amino, cyano, $C_{1-6}$alkyl, trifluoromethyl, $C_{1-6}$alkyloxy, mono- and di($C_{1-4}$alkyl)amino; or (c) one or more of $Ar^2$ is phenyl or phenyl substituted with up to 3 substituents, or with up to 2 substituents, or with one substituent, selected from halo, hydroxy, hydroxy$C_{1-6}$alkyl, trifluormethyl and $C_{1-6}$alkyloxy; or (d) one or more of $Ar^2$ is phenyl or phenyl substituted with up to 3 substituents, or with up to 2 substituents, or with one substituent, selected from the group consisting of halo, hydroxy, $C_{1-6}$alkyl, trifluoromethyl and $C_{1-6}$alkyloxy; or (e) one or more of $Ar^2$ is phenyl or phenyl substituted with up to 3 substituents, or with up to 2 substituents, or with one substituent, selected from halo, hydroxy, $C_{1-6}$alkyl and $C_{1-6}$alkyloxy; or (f) one or more of $Ar^2$ is phenyl or phenyl substituted with up to 3 substituents, or with up to 2 substituents, or with one substituent, selected from halo and $C_{1-6}$alkyl.

Further embodiments of the invention are compounds of formula (I) or any of the subgroups of compounds of formula (I) wherein one or more of $Ar^2$ is as specified for $Ar^1$. Still further embodiments of the invention are compounds of formula (I) or any of the subgroups of compounds of formula (I) wherein one or more of $Ar^1$ is phenyl.

Certain embodiments of this invention are groups of compounds of formula (I) or subgroups of compounds of formula (I) as specified herein wherein $Ar^2$-containing radicals in $R^3$ and/or $R^4$ are as specified in (a)-(f) in a previous paragraph. Certain embodiments of this invention are groups of compounds of formula (I) or subgroups of compounds of formula (I) as specified herein wherein $Ar^2$ in $R^1$ is as specified in (a)-(f) in a previous paragraph.

Subgroups X of the compounds of formula (I) are those compounds of formula (I), or any subgroup of compounds of formula (I) specified herein, such as the subgroups I, II, III, IV, V, VI, VII, VIII and IX mentioned above, wherein (a) Het is pyridyl, pyrazinyl, pyrimidinyl, furanyl, thienyl, pyrrolyl, thiazolyl, oxazolyl, imidazolyl, isothiazolyl, pyrazolyl, isoxazolyl, oxadiazolyl, quinolinyl, quinoxalinyl, benzimidazolyl, benzoxazolyl, benzthiazolyl;

(b) Net is pyridyl, pyrazinyl, pyrimidinyl, furanyl, thienyl, thiazolyl, oxazolyl;

(c) Net is pyridyl.

The compounds of formula (I) or any of the subgroups thereof can be prepared by reacting a benzimidazole derivative of formula (II) with an amine of formula (III) as in the following reaction scheme.

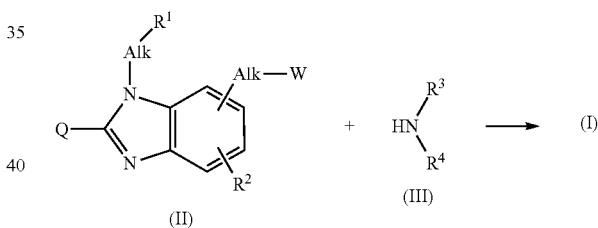

In this scheme Q, Alk, $R^1$, $R^2$, $R^3$, $R^4$ have the meanings defined above for the compounds of formula (I) or of any of the subgroups thereof. W is an appropriate leaving group, such as tosylate, mesylate or halo, preferably it is chloro or bromo. The reactions of these schemes may be conducted in a suitable solvent in the presence of a base such as an alkali metal carbonate or hydroxide, e.g. sodium, potassium or cesium carbonate; or an organic base such as a trialkylamine, e.g. triethylamine. Suitable solvents for this reaction are for example ethers, e.g. THF, dioxane; halogenated hydrocarbons, e.g. dichloromethane, $CHCl_3$, toluene, polar aprotic solvents such as DMF, DMSO, DMA and the like.

The compounds of formula (I) can also be prepared via a reductive amination process starting from an aldehyde or ketone of formula (IV) wherein Alk' has the same meaning of the radical Alk, but lacks one hydrogen atom. The intermediate (IV) is reacted with the amine (III) in the presence of a reducing agent such as hydrogen in the presence of a noble metal catalyst or a hydride such as a borohydride, e.g. sodium cyanoborohydride. The reductive amination reaction preferably is conducted in a suitable solvent such as an alcohol, e.g. methanol or ethanol, or an ether, e.g. THF or dioxane.

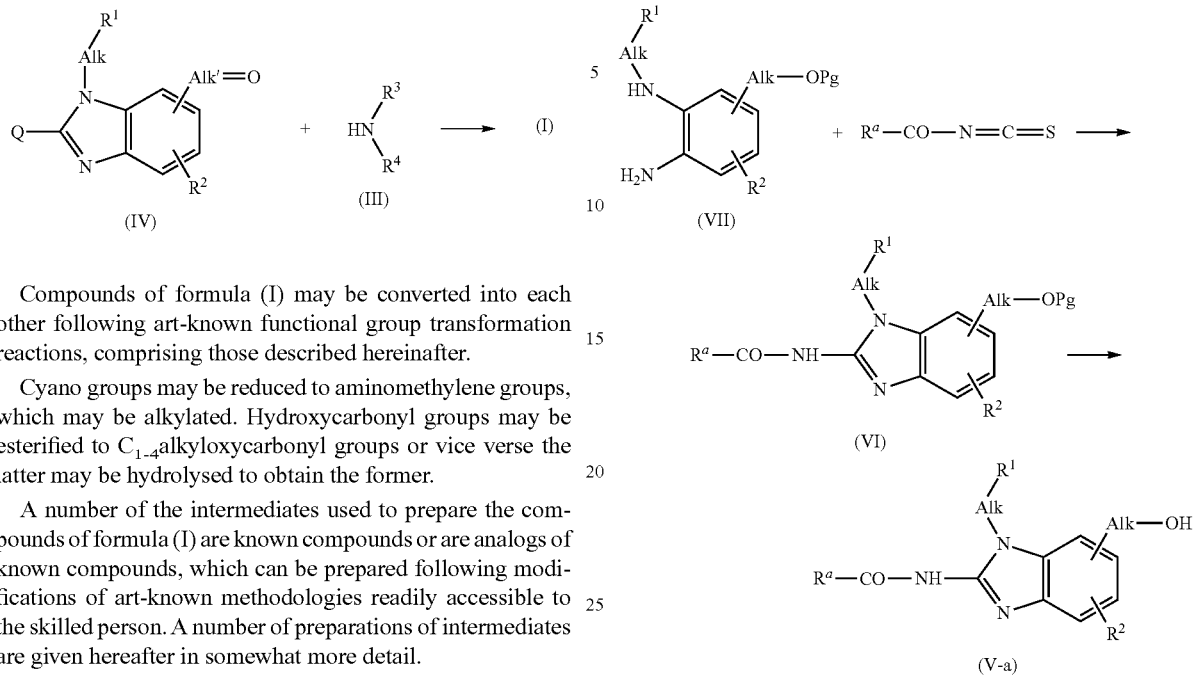

Compounds of formula (I) may be converted into each other following art-known functional group transformation reactions, comprising those described hereinafter.

Cyano groups may be reduced to aminomethylene groups, which may be alkylated. Hydroxycarbonyl groups may be esterified to $C_{1-4}$alkyloxycarbonyl groups or vice verse the latter may be hydrolysed to obtain the former.

A number of the intermediates used to prepare the compounds of formula (I) are known compounds or are analogs of known compounds, which can be prepared following modifications of art-known methodologies readily accessible to the skilled person. A number of preparations of intermediates are given hereafter in somewhat more detail.

The intermediates of formula (II) can be prepared from the corresponding hydroxyalkyl substituted benzimidazoles of formula (V) by reacting the latter with a suitable leaving group introducing agent such as a halogenating agent, e.g. $SOCl_2$, whereby the hydroxyalkyl group is converted to the corresponding haloalkyl group.

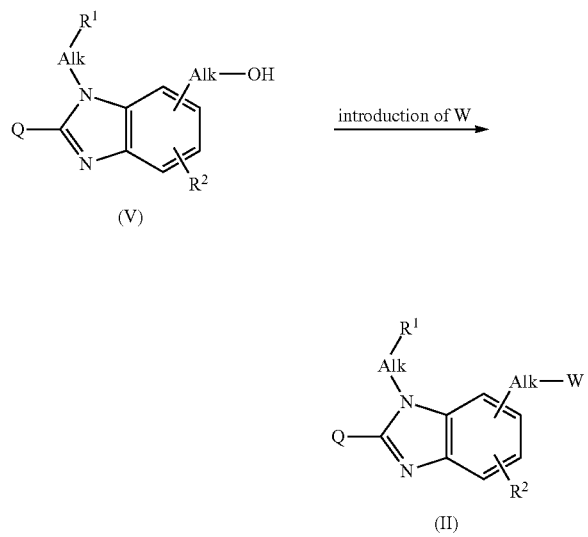

The intermediates (V) wherein Q is $C_{1-6}$alkylcarbonylamino, said intermediates being represented by formula (V-a), can be obtained by condensing $C_{1-6}$alkylcarbonyl thiocyanate with a diaminobenzene derivative (VII) wherein Pg is a hydroxyl protecting group, e.g. benzyl or a triallylsilyl group such as dimethyl t.butylsilyl. The protecting group in the thus obtained benzimidazole derivative (VI) is removed after the condensation reaction or may be removed in a further step of the synthesis procedures.

The intermediates (V) wherein Q is hydroxy can be obtained by condensing a reagent W—CO—W, wherein W is a leaving group such as the leaving groups defined above or imidazole or similar ring that can function as a leaving group, with a diaminobenzene derivative (VII). The protecting group on the hydroxy group is removed after the condensation reaction or may be removed in a further step of the synthesis procedures. The thus obtained 2-hydroxybenzimidazole derivatives can be etherified to the corresponding 2-$C_{1-6}$alkyloxybenzimidazole derivatives with a $C_{1-6}$alkyl halide or sulfate. The 2-hydroxy group can also be converted to the corresponding 2-W-substituted benzimidazole analogs wherein W again is a leaving group such as halo, e.g. chloro or bromo, and the thus obtained product can be converted to the 2-cyano-benzimidazole analogs by a substitution reaction with a cyanide, e.g. with sodium or potassium cyanide.

The intermediates (V) wherein Q is carboxyl can be obtained by condensing an oxalic acid derivative W—COCO—W with a diaminobenzene derivative (VII), wherein W is a leaving group such as the leaving groups defined above or one of W may also be a $C_{1-6}$alkoxy group. Also here, the protecting group on the hydroxy group is removed after the condensation reaction or may be removed in a further step of the synthesis procedures. The thus obtained 2-carboxylbenzimidazole derivatives can be esterified to the corresponding 2-$C_{1-6}$alkyloxycarbonylbenzimidazole derivatives, e.g. by reaction with an alcohol in the presence of a dehydrating agent such as sulfonyl chloride. The 2-$C_{1-6}$alkyloxycarbonyl group can be converted to the corresponding 2-aminocarbonyl, 2-$C_{1-6}$alkylaminocarbonyl or 2-di$C_{1-6}$alkylaminocarbonyl groups by reaction of the ester with ammonia or a mono- or di di$C_{1-6}$alkylamine. The intermediates (V) wherein Q is trifluormethyl can be obtained in a similar manner by condensing (VII) with trifluoroacetic acid chloride or bromide.

The intermediates of formula (IV) can be obtained from the alcohols of formula (VIII) by an oxidation reaction with a mild oxidant, e.g. with $MnO_2$.

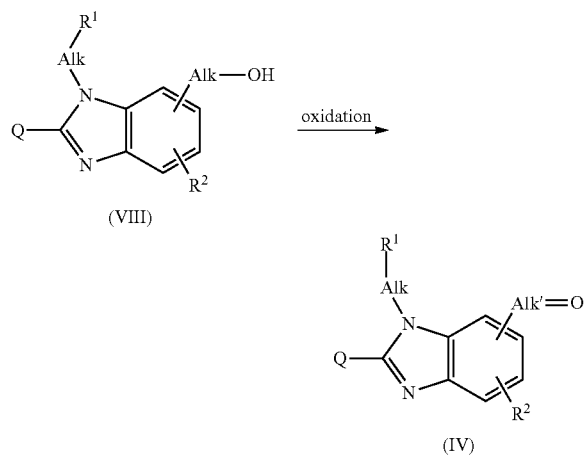

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., countercurrent distribution, liquid chromatography and the like.

The compounds of formula (I) as prepared in the hereinabove described processes are generally racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylactically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailability, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any subgroup thereof, their addition salts and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any subgroup thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the subgroups of compounds of formula (I), as specified herein.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

EXAMPLES

The following examples are intended to illustrate the present invention and not to limit it thereto. The terms 'compound a-11', 'compound b-7', etc. used in these examples refers to the same compounds in the tables.

The compounds were identified by LC/MS using the following equipment:

LCT: electrospray ionisation in positive mode, scanning mode from 100 to 900 amu; Xterra MS C18 (Waters, Milford, Mass.) 5 µm, 3.9×150 mm); flow rate 1 ml/min. Two mobile phases (mobile phase A: 85% 6.5 mM ammonium acetate+ 15% acetonitrile; mobile phase B: 20% 6.5 mM ammonium acetate+80% acetonitrile) were employed to run a gradient from 100% A for 3 min to 100% B in 5 min., 100% B for 6 min to 100% A in 3 min, and equilibrate again with 100% A for 3 min).

ZQ: electrospray ionisation in both positive and negative (pulsed) mode scanning from 100 to 1000 amu; Xterra RP C18 (Waters, Milford, Mass.) 5 µm, 3.9×150 mm); flow rate 1 ml/min. Two mobile phases (mobile phase A: 85% 6.5 mM ammonium acetate+15% acetonitrile; mobile phase B: 20% 6.5 mM ammonium acetate+80% acetonitrile) were employed to run a gradient condition from 100% A for 3 min to 100% B in 5 min., 100% B for 6 min to 100% A in 3 min, and equilibrate again with 100% A for 3 min).

Example 1

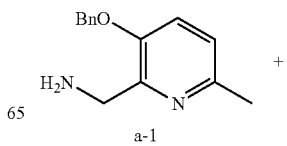

Scheme A

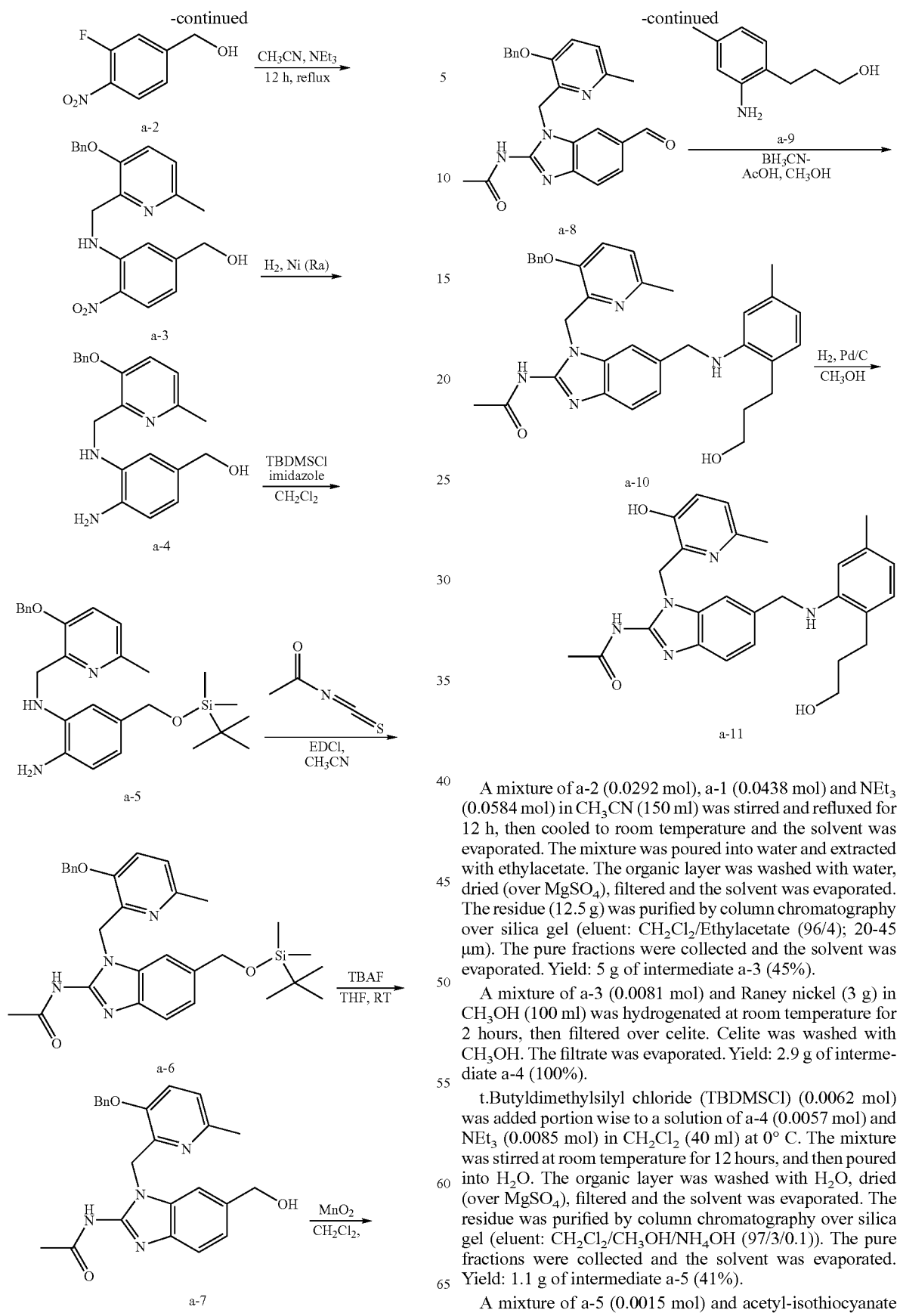

A mixture of a-2 (0.0292 mol), a-1 (0.0438 mol) and NEt$_3$ (0.0584 mol) in CH$_3$CN (150 ml) was stirred and refluxed for 12 h, then cooled to room temperature and the solvent was evaporated. The mixture was poured into water and extracted with ethylacetate. The organic layer was washed with water, dried (over MgSO$_4$), filtered and the solvent was evaporated. The residue (12.5 g) was purified by column chromatography over silica gel (eluent: CH$_2$Cl$_2$/Ethylacetate (96/4); 20-45 µm). The pure fractions were collected and the solvent was evaporated. Yield: 5 g of intermediate a-3 (45%).

A mixture of a-3 (0.0081 mol) and Raney nickel (3 g) in CH$_3$OH (100 ml) was hydrogenated at room temperature for 2 hours, then filtered over celite. Celite was washed with CH$_3$OH. The filtrate was evaporated. Yield: 2.9 g of intermediate a-4 (100%).

t.Butyldimethylsilyl chloride (TBDMSCl) (0.0062 mol) was added portion wise to a solution of a-4 (0.0057 mol) and NEt$_3$ (0.0085 mol) in CH$_2$Cl$_2$ (40 ml) at 0° C. The mixture was stirred at room temperature for 12 hours, and then poured into H$_2$O. The organic layer was washed with H$_2$O, dried (over MgSO$_4$), filtered and the solvent was evaporated. The residue was purified by column chromatography over silica gel (eluent: CH$_2$Cl$_2$/CH$_3$OH/NH$_4$OH (97/3/0.1)). The pure fractions were collected and the solvent was evaporated. Yield: 1.1 g of intermediate a-5 (41%).

A mixture of a-5 (0.0015 mol) and acetyl-isothiocyanate (0.0017 mol) in CH$_3$CN (15 ml) was stirred at room temperature for 12 hours. EDCI (0.0017 mol) was added. The mixture was stirred and refluxed for 4 hours, poured into H₂O and extracted with ethylacetate. The organic layer was separated, dried (over MgSO₄), filtered and the solvent was evaporated. The residue (0.9 g) was purified by column chromatography over silica gel (eluent: CH₂Cl₂/CH₃OH/NH₄OH (97/3/0.1)). The pure fractions were collected and the solvent was evaporated. The residue (0.4 g) was crystallized from 2-propanone. The precipitate was filtered off and dried. Yield: 0.28 g of intermediate a-6 (42%, melting point: 206° C.).

TBAF (0.0019 mol) was added drop wise at room temperature to a solution of a-6 (0.0006 mol) in THF (5 ml). The mixture was stirred at room temperature for 4 hours, then poured into H₂O and extracted with ethylacetate. The organic layer was washed with H₂O, dried (over MgSO₄), filtered and the solvent was evaporated. Yield: 0.3 g of intermediate a-7 (100%).

MnO₂ (2.7 g) was added portion wise at room temperature to a solution of a-7 (0.0006 mol) in CH₂Cl₂ (20 ml). The mixture was stirred at room temperature for 1 hour, and then filtered over celite. Celite was rinsed with CH₂Cl₂. The filtrate was evaporated. Yield: 0.19 g of intermediate a-8 (70%, melting point: 225° C.). CH₃CO₂H (5 drops) then BH₃CN— on solid support (0.0009 mol) were added at room temperature to a solution of a-8 (0.0004 mol) and a-9 (0.0006 mol) in CH₃OH (5 ml). The mixture was stirred at room temperature for 24 hours, then filtered and rinsed with CH₂Cl₂/CH₃OH. The organic layer was washed with NaHCO₃ 10% in water, dried (over MgSO₄), filtered and the solvent was evaporated. Yielding: 0.4 g of intermediate a-10 (100%). This product was used directly in the next reaction step.

A mixture of a-10 (0.0005 mol) and Pd/C (0.1 g) in CH₃OH (20 ml) was hydrogenated at room temperature for 1 hour under a 3 bar pressure, then filtered over celite. Celite was rinsed with CH₃OH/CH₂Cl₂. The filtrate was evaporated. The residue (0.23 g) was purified by column chromatography over silica gel (eluent: CH₂Cl₂/CH₃OH/NH₄OH (90/10/0.5); 5 μm). The pure fractions were collected and the solvent was evaporated. The residue (0.055 g) was crystallized from 2-propanone. The precipitate was filtered off and dried. Yield: 0.028 g of final compound a-11 (23%, melting point: 204° C.).

Compounds a-12, a-13, a-14, a-15, a-16, a-17 and a-18, listed in the table hereafter, were prepared following analogous procedures.

Example 2

Scheme B

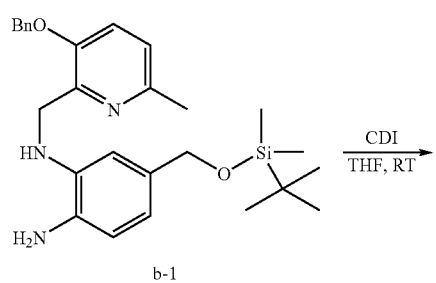

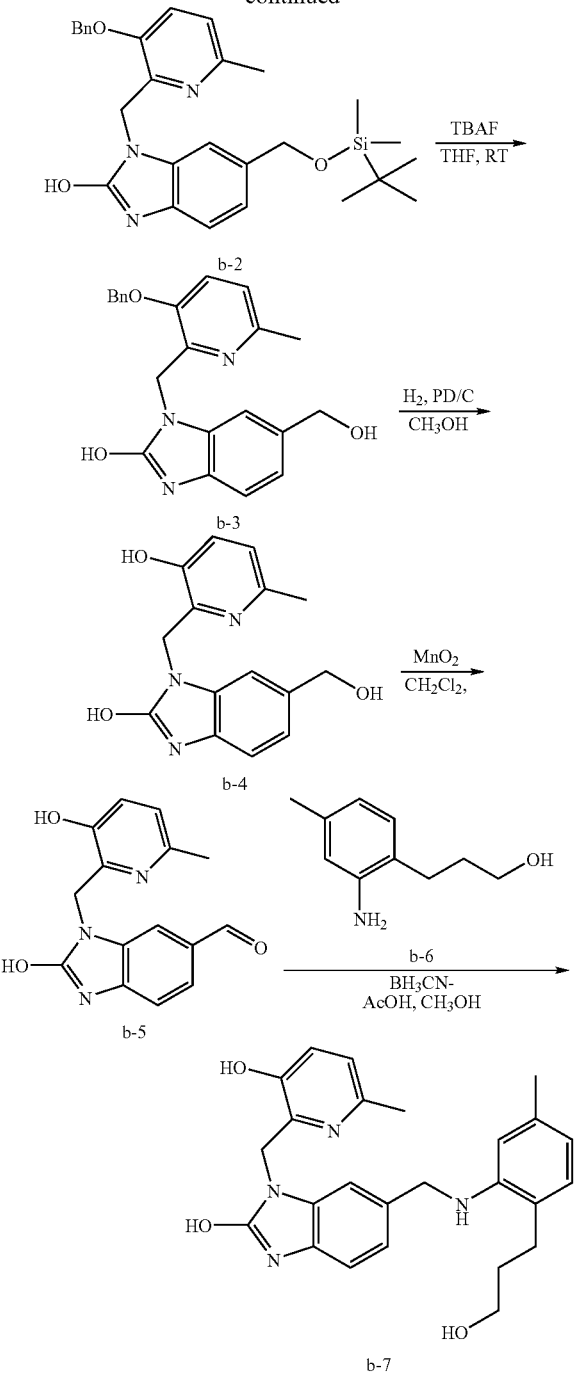

N,N'-carbonyl-diimidazole (0.0023 mol) was added at room temperature to a solution of b-1 (0.0021 mol) in THF (10 ml). The mixture was stirred at room temperature for 2 hours, and then poured into H₂O. CH₂Cl₂ was added. The organic layer was washed with a saturated solution of NaCl in water, dried (over MgSO₄), filtered and the solvent was evaporated. Yield: 1.1 g of intermediate b-2 (100%).

TBAF (0.0064 mol) was added drop wise at room temperature to a solution of b-2 (0.0021 mol) in THF (20 ml). The mixture was stirred at room temperature for 4 hours, poured into H₂O and extracted with ethylacetate. The organic layer was washed with H₂O, dried (over MgSO₄), filtered and the solvent was evaporated. The residue (1 g) was crystallized from 2-propanone. The precipitate was filtered off and dried. Yield: 0.53 g of intermediate b-3 (65%, melting point: 185° C.).

A mixture of b-3 (0.0011 mol) and Pd/C (0.2 g) in $CH_3OH$ (50 ml) was hydrogenated at room temperature for 1 hour under a 3 bar pressure, then filtered over celite. Celite was rinsed with $CH_2Cl_2/CH_3OH$. The filtrate was evaporated. Yield: 0.31 g of intermediate b-4 (95%).

$MnO_2$ (3.2 g) was added at room temperature to a mixture of b-4 (0.0011 mol) in $CH_2Cl_2$ (30 ml) and $CH_3CO_2H$ (6 ml). The mixture was stirred at room temperature for 3 hours, and then filtered over celite. Celite was rinsed with $CH_2Cl_2/CH_3OH$. The filtrate was evaporated. Yield: 0.6 g of intermediate b-5 (acetic acid salt, 100%).

$CH_3CO_2H$ (10 drops) then $BH_3CN$— on solid support (0.0026 mol) were added at room temperature to a mixture of b-5 (0.0013 mol) and b-6 (0.0019 mol) in $CH_3OH$ (7 ml). The mixture was stirred at room temperature for 48 hours, and then filtered over celite. Celite was rinsed with $CH_3OH$. The filtrate was evaporated. The residue (1 g) was purified by column chromatography over silica gel (eluent: $CH_2Cl_2/CH_3OH/NH_4OH$ (96/4/0.5); 10 μm). The pure fractions were collected and the solvent was evaporated. The residue (0.1 g) was crystallized from 2-propanone. The precipitate was filtered off and dried. Yield: 0.069 g of final compound b-7 (12%, melting point: 191° C.).

Compounds b-8, b-9, b-10, b-11, b-12, b-13, b-14 and b-15, listed in the table hereafter, were prepared following analogous procedures.

Example 3

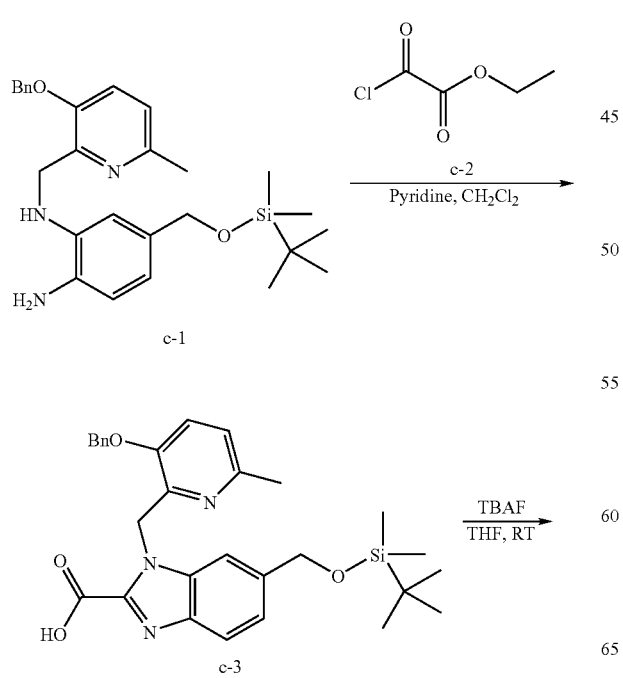

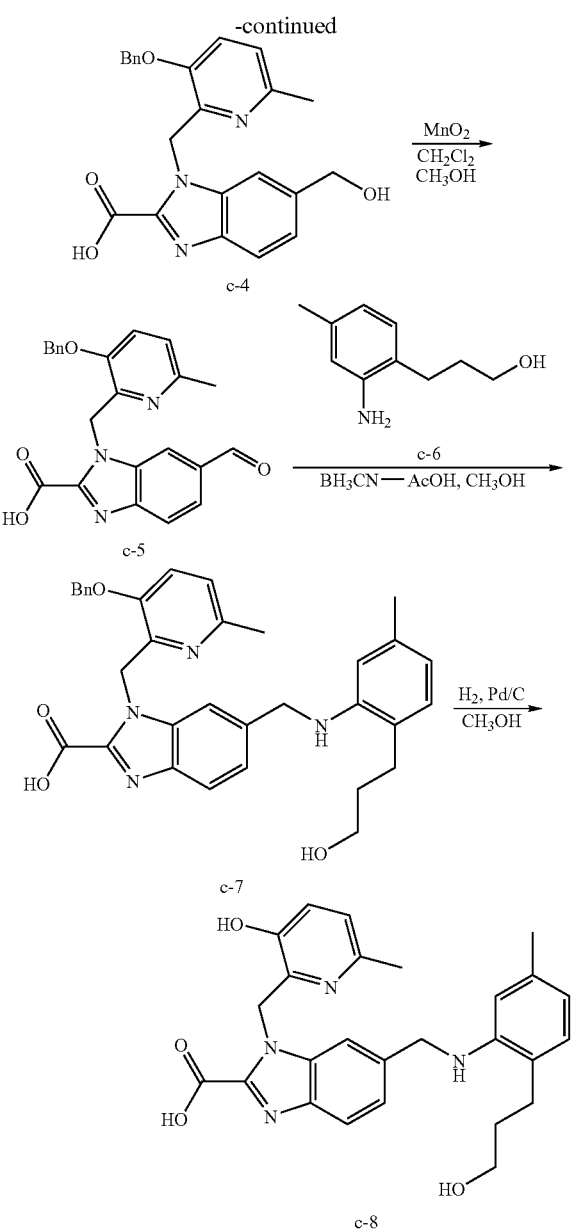

c-2 (0.0049 mol) was added drop wise to a solution of c-1 (0.0045 mol) and pyridine (0.0067 mol) in $CH_2Cl_2$ (50 ml) at 0° C. The mixture was stirred at room temperature for 12 hours and evaporated. The residue was purified by column chromatography over silica gel (eluent: $CH_2Cl_2/CH_3OH/NH_4OH$ (95/5/0.5)). The pure fractions were collected and the solvent was evaporated. Yield: 0.44 g of intermediate c-3 (19%).

TBAF (0.0014 mol) was added drop wise at room temperature to a solution of c-3 (0.0004 mol) in THF (10 ml). The mixture was stirred at room temperature for 3 hours, poured into $H_2O$ and extracted with ethylacetate. The organic layer was separated, dried (over $MgSO_4$), filtered and the solvent was evaporated. Yield: 0.3 g of intermediate c-4 (100%).

$MnO_2$ (2 g) was added portion wise at room temperature to a solution of c-4 (0.0004 mol) in $CH_2Cl_2$ (30 ml) and $CH_3OH$ (1 ml). The mixture was stirred at room temperature for 2 hours, and then filtered over celite. Celite was rinsed with CH$_2$Cl$_2$/CH$_3$OH. The filtrate was evaporated. Yielding: 0.19 g of intermediate c-5 (100%). This fraction was used directly in the next reaction step.

CH$_3$CO$_2$H (5 drops) then BH$_3$CN— on solid support (0.0009 mol) were added to a mixture of c-5 (0.0004 mol) and c-6 (0.0007 mol) in CH$_3$OH (5 ml). The mixture was stirred at room temperature for 48 hours, then filtered and rinsed with CH$_2$Cl$_2$/CH$_3$OH. The filtrate was evaporated. The residue (0.6 g) was purified by column chromatography over silica gel (eluent: CH$_2$Cl$_2$/CH$_3$OH/NH$_4$OH (93/7/0.5); 10 μm). The pure fractions were collected and the solvent was evaporated. Yield: 0.11 g of intermediate c-7 (42%).

A mixture of c-7 (0.0001 mol) and Pd/C (0.02 g) in CH$_3$OH (15 ml) and THF (3 ml) was hydrogenated at room temperature for 6 hours under atmospheric pressure, and then filtered over celite. Celite was rinsed with CH$_3$OH. The filtrate was evaporated. The residue (0.07 g) was purified by column chromatography over silica gel (eluent: CH$_2$Cl$_2$/CH$_3$OH/ NH$_4$OH (85/14/1); 5 μm). The pure fractions were collected and the solvent was evaporated. Yield: 0.01 g of final compound c-8 (14%).

Example 4

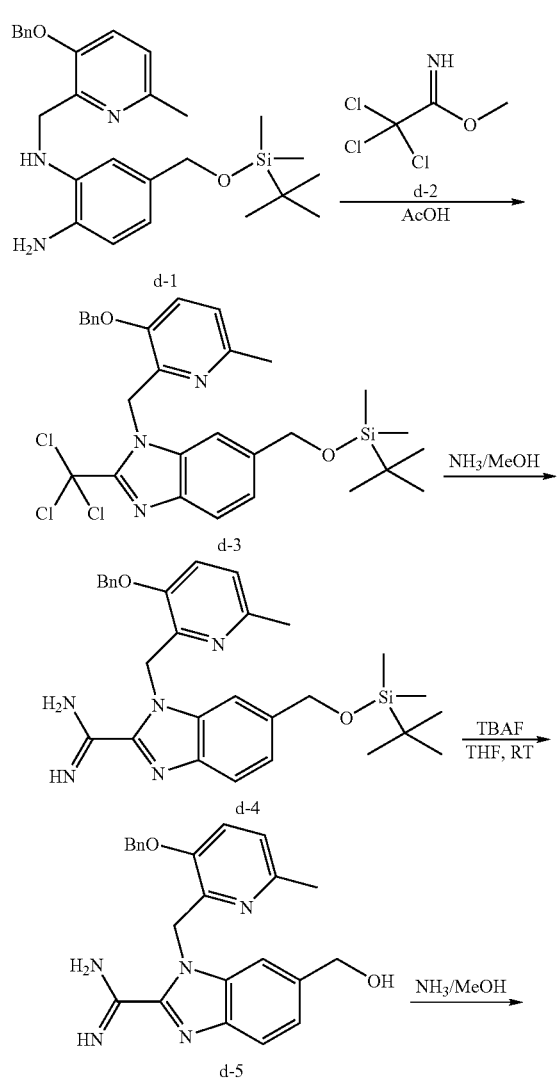

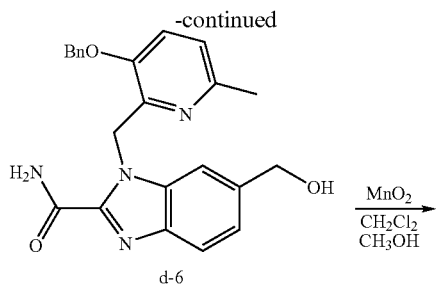

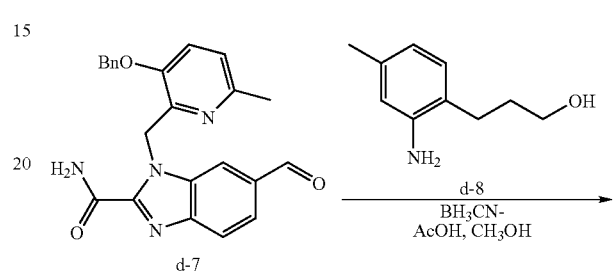

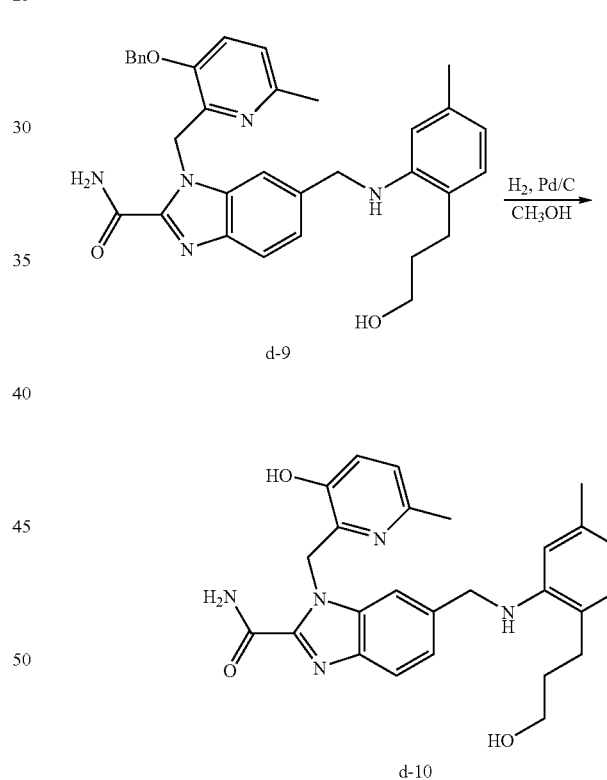

d-2 (0.0071 mol) was added portion wise to a solution of d-1 (0.0064 mol) in acetic acid (30 ml). The mixture was stirred at room temperature for 4 hours, then poured into ice, basified with K$_2$CO$_3$ and extracted with ethyl acetate. The organic layer was (eluent: CH$_2$Cl$_2$/CH$_3$OH/NH$_4$OH 84/16/ 1.6; 5 μm). The pure fractions were collected and the solvent was evaporated. The residue (0.084 g) was crystallized from 2-propanol/diethyl ether. The precipitate was filtered off and dried, yielding 0.061 g of final compound d-10 (62%, melting point: 216° C.).

The following table lists compounds that were prepared according to any one of the above examples.

| Comp. Nr. | Q | R¹ | R² | R³ | R⁴ | pEC$_{50}$ | MP (°C.) | LCMS (MH⁺) |
|---|---|---|---|---|---|---|---|---|
| a-11 | HN-C(=O)-CH₃ (acetamido) | -(CH₂)₃-OH | H | H | CH₃ | 8.4 | 204 | 474 |
| b-7 | HO- | -(CH₂)₃-OH | H | H | CH₃ | 7.75 | 191 | 433 |
| c-8 | HOOC- | -(CH₂)₃-OH | H | H | CH₃ | 6.3 | | 461 |
| b-8 | HO- | -(CH₂)₃-OH | H | H | H | 6.1 | | 419 |
| b-9 | HO- | H | Cl | H | Cl | 4 | | 429-433 |
| b-10 | HO- | H | CH₃ | H | H | 4 | | 375 |
| b-11 | HO- | H | -C≡CH | H | H | 4 | | 385 |
| b-12 | HO- | H | H | -S(=O)₂NH₂ | H | 5.65 | | 440 |
| b-13 | HO- | CH₃ | H | H | CH₃ | 5.45 | | 389 |
| b-14 | HO- | -(CH₂)₂-morpholino | H | H | H | 4 | | 474 |

-continued

| Comp. Nr. | Q | R¹ | R² | R³ | R⁴ | pEC$_{50}$ | MP (° C.) | LCMS (MH⁺) |
|---|---|---|---|---|---|---|---|---|
| b-15 | HO— | —CH$_2$CH$_2$C(O)NH$_2$ | H | H | H | 4 | | 432 |
| a-12 | CH$_3$C(O)NH— | —CH$_2$CH$_2$CH$_2$OH | H | H | H | 7.9 | | 460 |
| a-13 | CH$_3$C(O)NH— | H | Cl | H | Cl | 6.7 | | 470-474 |
| a-14 | CH$_3$C(O)NH— | H | CH$_3$ | H | H | 5.8 | | 416 |
| a-15 | CH$_3$C(O)NH— | H | —C≡CH | H | H | 6.4 | | 426 |
| a-16 | CH$_3$C(O)NH— | CH$_3$ | H | H | CH$_3$ | 7.2 | | 430 |
| a-17 | CH$_3$C(O)NH— | —CH$_2$CH$_2$-morpholinyl | H | H | H | 6.05 | | 515 |
| a-18 | CH$_3$C(O)NH— | —CH$_2$CH$_2$C(O)NH$_2$ | H | H | H | 6.25 | | 473 |
| d-10 | H$_2$NC(O)— | —CH$_2$CH$_2$CH$_2$OH | H | H | CH$_3$ | 6.2 | 216 | 460 |

The dotted line in the radicals listed in the above table represents the bond by which the radical is linked to the remainder of the molecule

Example 4

In Vitro Screening for Activity Against Respiratory Syncytial Virus

The percent protection against cytopathology caused by viruses (antiviral activity or $EC_{50}$) achieved by tested compounds and their cytotoxicity ($CC_{50}$) are both calculated from dose-response curves. The selectivity of the antiviral effect is represented by the selectivity index (SI), calculated by dividing the $CC_{50}$ (cytotoxic dose for 50% of the cells) by the $EC_{50}$ (antiviral activity for 50% of the cells).

Automated tetrazolium-based colorimetric assays were used for determination of $EC_{50}$ and $CC_{50}$ of test compounds. Flat-bottom, 96-well plastic microliter trays were filled with 180 µl of Eagle's Basal Medium, supplemented with 5 FCS (0% for FLU) and 20 mM Hepes buffer. Subsequently, stock solutions (7.8× final test concentration) of compounds were added in 45 µl volumes to a series of triplicate wells so as to allow simultaneous evaluation of their effects on virus- and mock-infected cells. Five five-fold dilutions were made directly in the microtiter trays using a robot system. Untreated virus controls, and HeLa cell controls were included in each test. Approximately 100 $TCID_{50}$ of Respiratory Syncytial Virus was added to two of the three rows in a volume of 50 µl. The same volume of medium was added to the third row to measure the cytotoxicity of the compounds at the same concentrations as those used to measure the antiviral activity. After two hours of incubation, a suspension ($4 \times 10^5$ cells/ml) of HeLa cells was added to all wells in a volume of 50 µl. The cultures were incubated at 37° C. in a 5% $CO_2$ atmosphere. Seven days after infection the cytotoxicity and the antiviral activity was examined spectrophotometrically. To each well of the microtiter tray, 25 µl of a solution of MTT (3-(4,5-dimethylthiazol-2-yl)-2,5-diphenyltetrazolium bromide) was added. The trays were further incubated at 37° C. for 2 hours, after which the medium was removed from each cup. Solubilization of the formazan crystals was achieved by adding 100 µl 2-propanol. Complete dissolution of the formazan crystals were obtained after the trays have been placed on a plate shaker for 10 min. Finally, the absorbances were read in an eight-channel computer-controlled photometer (Multiskan MCC, Flow Laboratories) at two wavelengths (540 and 690 nm). The absorbance measured at 690 nm was automatically subtracted from the absorbance at 540 nm, so as to eliminate the effects of non-specific absorption.

The results of this test are listed in the above table.

The invention claimed is:
1. A compound having the formula

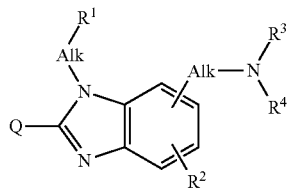

(I)

an addition salt or stereochemically isomeric form thereof, wherein

Q is hydroxy, $C_{1-6}$alkyloxy, $C_{1-6}$alkylcarbonylamino, $C_{1-6}$alkyloxycarbonylamino, carboxyl, $C_{1-6}$alkyloxycarbonyl, $C_{1-6}$alkylcarbonyl, cyano, aminocarbonyl, mono or di($C_{1-6}$alkyl)aminocarbonyl, polyhalo$C_{1-6}$alkyl;

each Alk independently represents $C_{1-6}$alkanediyl;

$R^1$ is $Ar^2$ or a monocyclic or bicyclic heterocycle selected from piperidinyl, piperazinyl, morpholinyl, thiomorpholinyl, pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]-pyridinyl, imidazo[1,2-a]pyridinyl and 2,3-dihydro-1,4-dioxino[2,3-b]pyridyl; wherein each of said monocyclic or bicyclic heterocycles may optionally be substituted with 1, 2, or 3 substituents each independently selected from the group consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, hydroxy$C_{1-6}$alkyl, mono- or di($C_{1-6}$alkyl)-amino, mono- or di($C_{1-6}$alkyl)amino$C_{1-6}$alkyl, polyhalo$C_{1-6}$alkyl, $C_{1-6}$alkyl-carbonylamino, $C_{1-6}$alkyloxycarbonyl, aminocarbonyl, mono- and di-$C_{1-6}$alkylaminocarbonyl;

$R^2$ is hydrogen or $C_{1-6}$alkyl;

$R^3$ and $R^4$ independently from each other are hydrogen, $C_{1-6}$alkyl, $Ar^2$, $Ar^2C_{1-6}$alkyl, $C_{1-6}$alkylcarbonyl, $Ar^2$carbonyl, $Ar^2C_{1-6}$alkylcarbonyl, $C_{1-6}$alkylsulfonyl, aminosulfonyl, $Ar^1$sulfonyl, $Ar^1C_{1-6}$alkylsulfonyl, $C_{1-6}$alkyloxy$C_{1-6}$alkyl, amino$C_{1-6}$alkyl, mono- or di($C_{1-6}$alkyl)amino$C_{1-6}$ alkyl, hydroxy$C_{1-6}$alkyl, aminocarbonyl$C_{1-6}$alkyl, $C_{1-6}$alkyloxycarbonyl$C_{1-6}$alkyl, hydroxycarbonyl-$C_{1-6}$alkyl, aminosulfonyl$C_{1-6}$alkyl, Het, Het-$C_{1-6}$alkyl, Het-carbonyl, Het-sulfonyl, Het$C_{1-6}$alkylsulfonyl and Het-$C_{1-6}$alkylcarbonyl;

$Ar^1$ is phenyl or phenyl substituted with 1 or more, such as 2, 3 or 4, substituents selected from halo, hydroxy, $C_{1-6}$alkyl, hydroxy$C_{1-6}$alkyl, polyhalo$C_{1-6}$alkyl, and $C_{1-6}$alkyloxy;

$Ar^2$ is phenyl or phenyl substituted with 1 or more, such as 2, 3, 4 or 5, substituents selected from halo, cyano, $C_{1-6}$alkyl, $C_{2-6}$alkenyl, $C_{2-6}$alkynyl, cyano$C_{1-6}$alkyl, cyano$C_{2-6}$alkenyl, cyano$C_{2-6}$alkynyl, $Ar^1$, $Ar^1C_{1-6}$alkyl, $R^{5b}$—O—, $R^{5b}$—S—, —N($R^{5a}R^{5b}$), polyhalo$C_{1-6}$alkyl, polyhalo$C_{1-6}$alkyloxy, $R^6$—C(=O)—, $R^{5b}$—O—C(=O)—, N($R^{5a}R^{5b}$)—C(=O)—, N($R^{5a}R^{5b}$)-sulfonyl, $R^{5b}$—O—$C_{1-6}$alkyl, $R^{5b}$—S—$C_{1-6}$alkyl, $R^6$—S(=O)$_2$—$C_{1-6}$alkyl, N($R^{5a}R^{5b}$)—$C_{1-6}$alkyl, $R^6$—C(=O)—$C_{1-6}$alkyl, $R^{5b}$—O—C(=O)—$C_{1-6}$alkyl, N($R^{5a}R^{5b}$)—C(=O)—$C_{1-6}$alkyl, $R^6$—C(=O)—NR$^{5b}$—, $R^6$—S(=O)$_2$-amino, $R^6$—C(=O)—O—, $R^6$—C(=O)—NR$^{5b}$—$C_{1-6}$alkyl, $R^6$—C(=O)—O—$C_{1-6}$alkyl;

$R^{5a}$ is hydrogen, $C_{1-6}$alkyl, $Ar^1$, $Ar^1C_{1-6}$alkyl, $C_{1-6}$alkylcarbonyl, $Ar^1$carbonyl, $Ar^1C_{1-6}$alkylcarbonyl, $C_{1-6}$alkylsulfonyl, $Ar^1$sulfonyl, $Ar^1C_{1-6}$alkylsulfonyl, $C_{1-6}$alkyloxy$C_{1-6}$alkyl, amino$C_{1-6}$alkyl, mono- or di($C_{1-6}$alkyl)amino$C_{1-6}$alkyl, hydroxy$C_{1-6}$alkyl, Het, Het-$C_{1-6}$alkyl, Het-carbonyl, Het-sulfonyl, Het-$C_{1-6}$alkyl-carbonyl;

$R^{5b}$ is hydrogen, $C_{1-6}$alkyl, $Ar^1$ or $Ar^1C_{1-6}$alkyl;
$R^6$ is $C_{1-6}$alkyl, $Ar^1$ or $Ar^1C_{1-6}$alkyl;
Het is a heterocycle being selected from tetrahydrofuranyl, tetrahydrothienyl, pyrrolidinyl, pyrrolidinonyl, furanyl, thienyl, pyrrolyl, thiazolyl, oxazolyl, imidazolyl, isothiazolyl, pyrazolyl, isoxazolyl, oxadiazolyl, thiadiazolyl, piperidinyl, homopiperidinyl, piperazinyl, morpholinyl, pyridyl, pyrazinyl, pyridazinyl, pyrimidinyl, tetrahydroquinolinyl, quinolinyl, isoquinolinyl, benzodioxanyl, benzodioxolyl, indolinyl, indolyl, each of said heterocycle may optionally be substituted with oxo, amino, $Ar^1$, $C_{1-6}$alkyl, amino$C_{1-6}$alkyl, $Ar^1C_{1-6}$alkyl, mono- or di($C_{1-6}$alkyl)amino$C_{1-6}$alkyl, mono- or di($C_{1-6}$ alkyl)amino, hydroxy$C_{1-6}$alkyl, $C_{1-6}$alkoxy$C_{1-6}$alkyl, cyano$C_{1-6}$alkyl, aminocarbonyl-$C_{1-6}$-alkyl, mono- or di($C_{1-6}$alkyl)aminocarbonyl-$C_{1-6}$-alkyl, carboxyl-$C_{1-6}$-alkyl, $C_{1-6}$alkoxy-carbonyl-$C_{1-6}$alkyl.

2. A compound according to claim 1 wherein the compound has the formula (I-a):

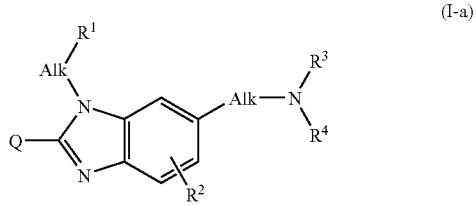

(I-a)

wherein Q, $R^1$, Alk and $R^2$, $R^3$ and $R^4$ are as claimed in claim 1.

3. A compound according to claims 1-2 wherein $R^1$ is pyridyl substituted with 1 or 2 substituents independently selected from the group consisting of hydroxy, $C_{1-6}$alkyl, halo, $C_{1-6}$alkyloxy, $Ar^1C_{1-6}$alkyloxy and ($C_{1-6}$alkyloxy)$C_{1-6}$alkyloxy.

4. A compound according to in any of claims 1-3, wherein each Alk is methylene.

5. A compound according to any of claims 1-4, wherein $R^2$ is hydrogen.

6. A compound according to any of claims 1-5, wherein $R^3$ is hydrogen, hydroxy-$C_{1-6}$alkyl, aminocarbonyl$C_{1-6}$alkyl, mono- and di($C_{1-6}$alkyl)aminocarbonyl$C_{1-6}$alkyl.

7. A compound according to any of claims 1-6, wherein $R^4$ is $Ar^2$.

8. A compound according to any of claims 1-7, wherein Q is hydroxy, $C_{1-6}$alkyloxy, $C_{1-6}$alkylcarbonylamino, carboxyl, aminocarbonyl, mono or di($C_{1-6}$alkyl)aminocarbonyl.

9. A pharmaceutical composition comprising a pharmaceutically acceptable carrier, and as active ingredient a therapeutically effective amount of a compound as claimed in any one of claims 1 to 8.

10. A process for preparing a compound as claimed in any of claims 1 to 8, said process comprising:

(a) reacting a benzimidazole derivative of formula (II) with an amine of formula (III) as in the following reaction scheme:

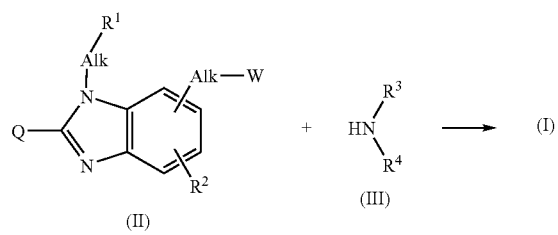

wherein W is an appropriate leaving group;

(b) conducting a reductive amination process starting from an aldehyde or ketone of formula (IV) wherein Alk' has the same meaning of the radical Alk, but lacks one hydrogen atom, which intermediate (IV) is reacted with the amine (III) in the presence of a reducing agent:

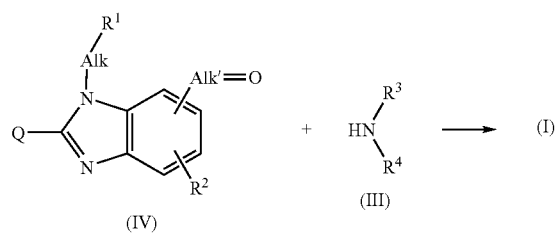

wherein in the above schemes Q, Alk, R1, R2, R3, R4 have the meanings defined in any of claims 1 to 8 above;

(c) converting a compound of formula (I) into its salt form by treatment with a base or acid or conversely converting a salt form of a compound of formula (I) into its free form by treatment with an acid or base.

* * * * *